US008025663B2

(12) United States Patent
Keeven et al.

(10) Patent No.: US 8,025,663 B2
(45) Date of Patent: Sep. 27, 2011

(54) AUGMENTS FOR SURGICAL INSTRUMENTS

(75) Inventors: Richard D. Keeven, Warsaw, IN (US);
Mari Truman, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 1126 days.

(21) Appl. No.: 10/748,449

(22) Filed: Dec. 30, 2003

(65) Prior Publication Data
US 2005/0143744 A1   Jun. 30, 2005

(51) Int. Cl.
*A61F 2/46* (2006.01)
(52) U.S. Cl. .................. 606/86 R; 606/88
(58) Field of Classification Search .......... 606/86, 606/99, 62–68, 87–88; 623/20.14, 20.16, 623/20.21, 20.28, 20.32–33
See application file for complete search history.

(56) References Cited

U.S. PATENT DOCUMENTS

| | | | | |
|---|---|---|---|---|
| 2,460,470 A | * | 2/1949 | Rogers | 606/86 |
| 4,487,203 A | * | 12/1984 | Androphy | 606/88 |
| 4,653,488 A | * | 3/1987 | Kenna et al. | 606/88 |
| 4,721,104 A | * | 1/1988 | Kaufman et al. | 606/88 |
| 4,738,254 A | * | 4/1988 | Buechel et al. | 606/96 |
| 5,275,603 A | * | 1/1994 | Ferrante et al. | 606/86 R |
| 5,425,490 A | * | 6/1995 | Goble et al. | 227/175.1 |
| 5,462,550 A | * | 10/1995 | Dietz et al. | 606/86 |
| 5,464,406 A | * | 11/1995 | Ritter et al. | 606/86 |
| 5,520,695 A | | 5/1996 | Luckman | |
| 5,639,113 A | * | 6/1997 | Goss et al. | 280/728.2 |
| 5,649,929 A | | 7/1997 | Callaway | |
| 5,653,714 A | * | 8/1997 | Dietz et al. | 606/87 |
| 5,683,469 A | * | 11/1997 | Johnson et al. | 623/20.32 |
| 5,733,290 A | * | 3/1998 | McCue et al. | 606/86 |
| 5,735,904 A | | 4/1998 | Pappas | |
| 5,788,701 A | * | 8/1998 | McCue | 606/88 |
| 5,931,838 A | * | 8/1999 | Vito | 606/281 |
| 5,938,665 A | | 8/1999 | Martin | |
| 5,976,147 A | * | 11/1999 | LaSalle et al. | 606/88 |
| 6,056,754 A | | 5/2000 | Haynes et al. | |
| 6,096,082 A | | 8/2000 | Stegmüller et al. | |
| 6,159,215 A | * | 12/2000 | Urbahns et al. | 606/86 |
| 6,443,991 B1 | | 9/2002 | Running | |
| 6,458,135 B1 | | 10/2002 | Harwin et al. | |
| 6,575,980 B1 | | 6/2003 | Robie et al. | |
| 6,746,454 B2 | * | 6/2004 | Winterbottom et al. | 606/99 |

(Continued)

FOREIGN PATENT DOCUMENTS
EP    0 919 195    6/1999
(Continued)

OTHER PUBLICATIONS

Merriam Webster® online definition of couple (attached hereto). Retrieved from the Internet: <URL: http://www.m-w.com>.*

(Continued)

*Primary Examiner* — Nicholas Woodall
(74) *Attorney, Agent, or Firm* — Maginot, Moore & Beck

(57) ABSTRACT

A system for establishing a prosthetic gap between first and second bones at a joint comprises an instrument for positioning within the gap between the first and second bones, and an augment for filling the gap when coupled to the instrument. In one embodiment, a resilient coupling member is provided to resiliently and removably couple the augment to the instrument. In another embodiment, the instrument and augment are configured so that the augment can be coupled to the instrument on either one of opposite surfaces of the augment facing the first and second bones.

20 Claims, 3 Drawing Sheets

U.S. PATENT DOCUMENTS

| | | | |
|---|---|---|---|
| 6,755,841 B2 * | 6/2004 | Fraser et al. | 606/99 |
| 2002/0058950 A1 * | 5/2002 | Winterbottom et al. | 606/99 |
| 2002/0116009 A1 * | 8/2002 | Fraser et al. | 606/99 |
| 2003/0236525 A1 * | 12/2003 | Vendrely et al. | 606/87 |

FOREIGN PATENT DOCUMENTS

| | | |
|---|---|---|
| JP | 11221244 A | 8/1999 |
| WO | WO97/21389 | 6/1997 |
| WO | WO98/25526 | 6/1998 |
| WO | WO99/09900 | 3/1999 |
| WO | 03013373 A1 | 2/2003 |

OTHER PUBLICATIONS

Australian Patent Office Examiner's first report, corresponding to Application No. 2004242486, mailed on Jul. 28, 2009, 2 pages.

Japanese Office Action in corresponding Japanese patent application (i.e., 2004-380767, mailed Jul. 6, 2010), 4 pages.

* cited by examiner

AUGMENTS FOR SURGICAL INSTRUMENTS

BACKGROUND OF THE INVENTION

The present invention relates to devices for use in orthopaedic surgery, and especially for proper alignment of surgical instruments used in preparing a bone for an implant. The invention has particular application in preparing the distal end of the femur to receive a femoral prosthesis.

Damage or disease can deteriorate the bones, articular cartilage and ligaments of human joints, such as the knee, which can ultimately affect the ability of the natural joint to function properly. To address these conditions, prosthetic joints have been developed that are mounted to prepared ends of the bones of the joint, namely the tibia and femur in the case of a knee prosthesis. Among the many knee prostheses, a mobile bearing knee simulates the condylar and bearing surfaces of the knee to emulate the natural movement of the knee during flexion and extension. The tibial component is configured to permit rotation about the axis of the tibia to accurately replicate the effects of differential rollback in the transverse plane.

Implantable mobile bearing knee prostheses, such as the prosthesis 10 shown in FIG. 1, for diseased and/or damaged knees typically include three components, namely a tibial component 12, a femoral component 16 and a meniscal component (not shown). The tibial component 12 includes a platform 13 with a stem 14 configured for engagement in the prepared proximal end of the tibia. Generally, in a total knee joint replacement the platform 13 replaces the entire superior surface of the tibial plateau and substitutes for the tibial condylar surfaces. The femoral component can also include laterally-spaced condylar portions joined by an inter-condylar bridge and a patellar surface.

The femoral component 16 defines interior mounting surfaces 17 that often require involved cuts into the distal end of the femur. Since the components of the mobile bearing knee prosthesis 10 are generally configured to restore or emulate as much of the natural motion of the knee joint as possible, the femoral component often has a complicated geometry, which requires significant modification to the femur to accept and support the implant. The selection of the particular prosthesis components is usually dictated by the condition of the patient's knee. For instance, the condition of the distal end of the femur and proximal end of the tibia, as well as the patency of the surrounding ligaments and soft tissue can affect the form of the joint prosthesis.

In addition to the overall implant geometry, implant positioning with respect to the natural bone is critical. For instance, a proper implant will maintain the proper tension in the retained ligaments supporting the joint. In total knee reconstruction surgery, the menisci, bone ends and other stabilizing tissues are removed and replaced with implants. The thicknesses of the implants are ideally equal to the thickness of the removed material. Exceptions occur in reconstruction of severe deformity, where ligament length and tension after tissue releases during the reconstruction vary significantly form the preoperative state and from the normal knee.

Intraoperatively, the gap between the facing ends of the bones of the joint, which are related to the final implant position, can be manipulated. In the knee, a critical measure is the gap when the knee is in flexion or extension. The bone gaps in an ideal surgical reconstruction will have be the same in flexion and extension, the only exception being with implant systems having uneven implant thicknesses between anterior and posterior, or between medial and lateral compartments on either the tibial or femoral implants. The bone gaps for implants with unequal thicknesses must be accommodated for by the measuring tool or in the measurements when accessing potential implant fit. An ideal implant will maintain the same tension in flexion and extension, and the resulting joint tension and the stability of the implant will be substantially identical to the joint tension and stability of the patient's natural knee.

In preparing a knee joint, for instance, to receive a prosthesis, the orthopaedic surgeon typically uses templates to determine the proper size of the implant components. The surgeon may also measure the joint gap and choose a spacer that can be used in the procedure to maintain that gap. Since the femoral component of the knee prosthesis requires complex cuts in the femur, a femoral resection guide is used, such as the resection guide 20 shown in FIG. 2. The main body 22 of the guide 20 is aligned at the distal end of the femur F and held in place by one or more guide pins 24. The resection guide 20 may include other structure and components for maintaining the guide in a proper orientation as the femur is resected.

In order to ensure that the resulting femoral implant achieves the proper flexion and extension gaps, a femoral positioner 26 is often used. The femoral positioner shown in FIG. 2 includes a surface alignment plate 28 that rests on the previously resected surface R of the tibia. The alignment plate 28 is integral with a connector plate 30 that fits within a slot 23 in the main body 22 of the resection guide 20. The femoral positioner 26 is thus used to help position the resection guide so that the femur is properly resected.

Another known femoral resection guide 32 is depicted in FIG. 3. This guide includes a body 33 defining a slot 34 for receiving a saw. A stylus 36 is used to align the depth of the saw cut. Handles 40 can be provided to help stabilize the resection guide during a cut. Guide pins 38 extend into the femur F to align and support the resection guide.

It is important that the resection guide be properly oriented when the distal end of the femur is prepared, otherwise the femoral implant will be produce undue strain or laxity in the knee joint. It is critical to maintain equal flexion and extension gaps to restore the proper anatomic tension as much as possible, regardless of the nature of the knee prosthesis. For instance, most mobile bearing knees are modular, meaning that several bearing elements can be provided depending upon the patient's anatomy. Obviously, thicker bearing elements correspond to greater flexion/extension gaps.

Similar modularity is important in the guide instruments used to ensure proper manipulation of the bones of the joint. There is a need, therefor, for an augment that can be readily used in the orthopaedic procedure to allow the guide instruments to properly emulate the natural anatomy of the instrumented joint.

Moreover, there is a need for an augment that can account for variations in the quality of the underlying bone. This need is particularly acute for revision surgeries in which the bone may have defects that make finding a stable platform difficult.

SUMMARY OF THE INVENTION

In one embodiment of the invention a system is provided for establishing a prosthetic gap between first and second bones at a joint. The system comprises an instrument for positioning within the gap between the first and second bones, the instrument having a first surface facing the first bone and a second surface facing the second bone. The system further comprises an augment for filling the gap when coupled to the instrument.

The augment and instrument include a mating connection mechanism that permits ready mounting and removal of the augment to the instrument. In certain embodiments, the instrument defines at least one bore between the first and second surfaces and the augment includes at least one pin sized to be received within the at least one bore with the augment in contact with either the first surface or the second surface. Other mating connection mechanisms can include other male-female constructs, such as dovetail or snap-fit mechanisms, or a canted coil spring mechanism.

In one specific embodiment, the instrument is a femoral positioner that includes a surface alignment plate configured to engage the tibia and a connector plate configured to engage a femoral resection guide. The surface alignment plate defines the at least one bore and is contacted by a mating surface of the augment form which the pin projects. In another specific embodiment, the instrument is a spacer block having a spacer body and a handle projecting therefrom. The spacer block defines the at least one bore.

In one aspect of the invention, the bore includes a resilient member disposed therein. The resilient member is configured to resiliently engage the pin when the pin extends through the bore. In one embodiment, the bore defines an internal groove, and the resilient member is an O-ring mounted within the groove. In an alternative embodiment, the bore defines a pair of internal grooves, one each adjacent each of the first and second surfaces, and the resilient member includes an O-ring mounted within each of the pair of grooves.

The augment includes a mating surface for contacting the instrument when the pin is within the bore, and an opposite surface. In certain embodiments, the opposite surface is substantially parallel to the first or second surface of the instrument. In other embodiments, the opposite surface defines a contour substantially similar to the contour of the first or second bones.

In another embodiment of the invention, a system for establishing a prosthetic gap between first and second bones at a joint comprises an instrument for positioning within the gap between the first and second bones, an augment for filling the gap when coupled to the instrument, and means for removably coupling the augment to the instrument including a resilient member disposed between the augment and the instrument. In one embodiment, the means for removably coupling includes a bore defined in the instrument and a pin disposed on the augment sized for engagement within the bore, with the resilient member disposed within the bore. The resilient member can be one or more O-rings disposed within the bore.

The illustrated embodiment is used for a knee prosthesis. However, it is contemplated that the present invention can be used in other human joints that may benefit from the features of the present invention.

It is one object of the invention to provide an augment that can serve as a spacer or a shim as part of a system for establishing a prosthetic gap for a human joint. Another object is to provide an augment that can be readily and securely mounted and disengaged from an instrument used in the system for establishing a prosthetic gap.

A further object resides in features of the invention that allow the augment to be mounted on different surfaces of the instrument to contact different bones of the joint. These and other objects and benefits of the invention can be discerned from the following written description, taken together with the accompanying figures

DESCRIPTION OF THE PREFERRED EMBODIMENTS

Figure 1:
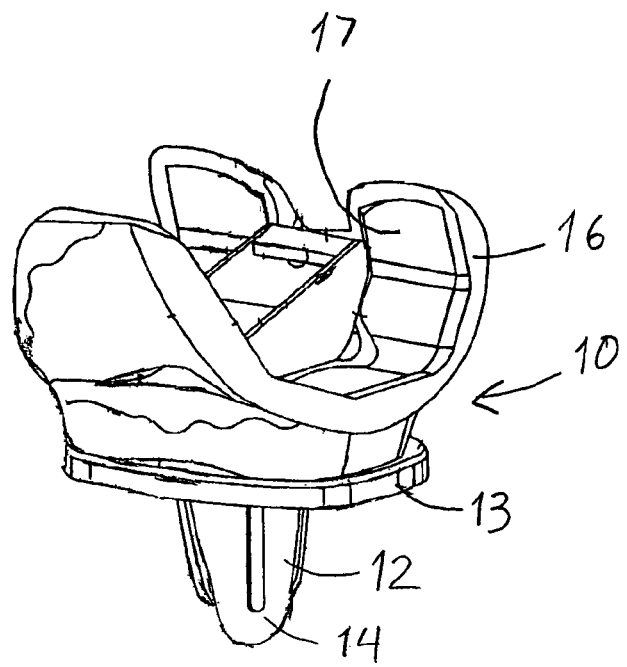
FIG. 1 is a perspective view of one type of knee prosthesis.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
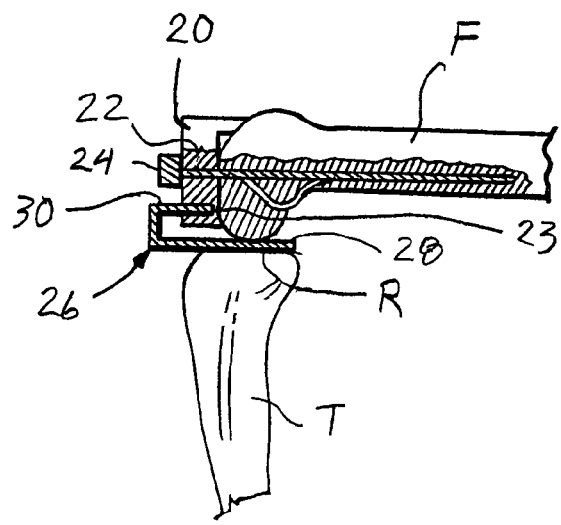
FIG. 2 is a side representation of a femoral resection guide as it is being positioned on the femur.
Figure 3:
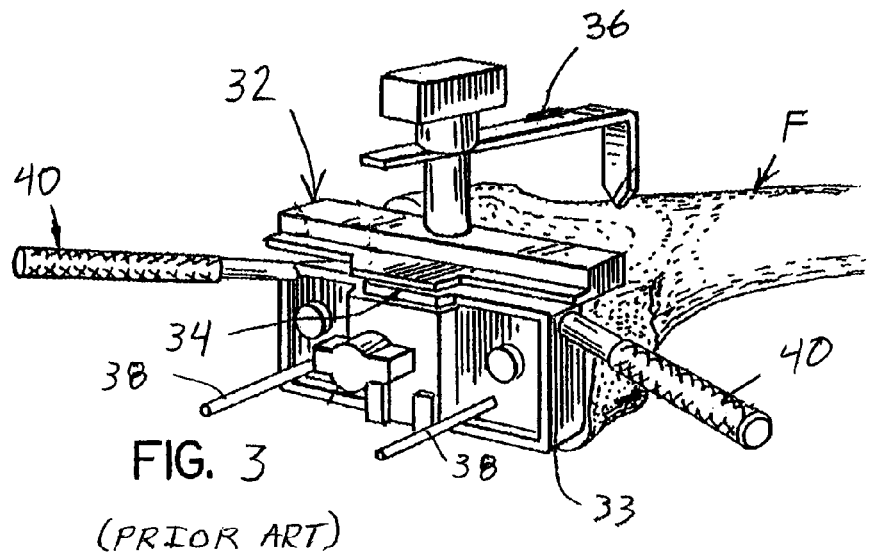
FIG. 3 is a perspective view of another known femoral resection guide.
Figure 4:
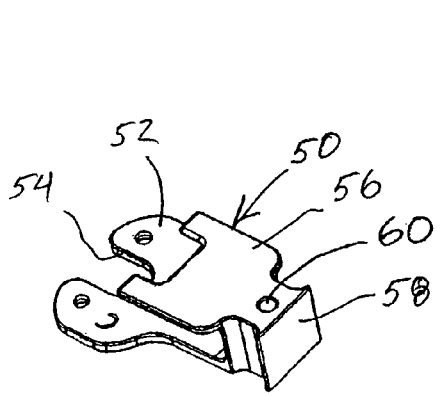
FIG. 4 is a perspective view of a femoral positioner according to one embodiment of the invention.
Figure 5:
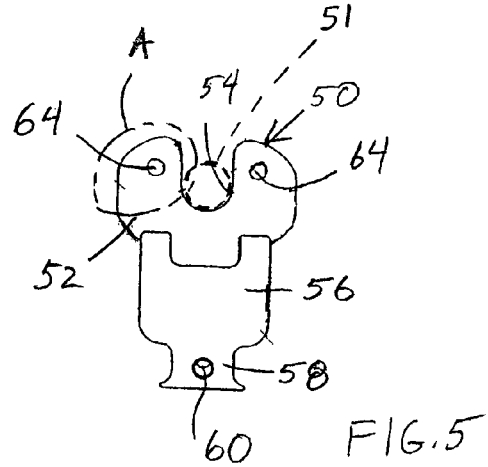
FIG. 5 is a top elevational view of the femoral positioner shown in FIG. 4.

In accordance with one aspect of the present invention, a femoral positioner 50 is provided that can be used with a femoral resection guide, such as the guides 20 and 32 depicted in FIGS. 2 and 3. The positioner 50 includes a surface alignment plate 52 that is configured to rest on the resected surface R of the tibia T, like the positioner 26 shown in FIG. 2. The alignment plate 52 defines a slot 54 that can engage a pin 51 disposed within the medullary canal of the tibia (not shown) to align the plate with the resected tibial plateau in a known manner.

A connector plate 56 is arranged parallel with the surface alignment plate 52 and is configured to engage a mating feature in the resection guide. For instance, the connector plate 56 can engage the slot 23 in the main body of the resection guide 20 shown in FIG. 2, or the slot 34 or other mating feature in the guide 32. A base 58 integrally spans between the plates 52, 56 and establishes the distance between these two parallel plates. The base thus sets the distance between the surface of the tibia and a reference point by which the position of the resection guide is established. The base 58 can define a bore 60 therethrough to receive an alignment rod (not shown) that can be used to check ligament tension during the instrumentation procedure.

The goal of the femoral positioner 50 is to properly orient the femur relative to the resected end R of the tibia. When the femur is properly positioned, the resection guide can be mounted on the exposed end of the femur and the necessary cuts made at the proper location on the bone. While the positioner 50 may be properly sized to achieve these results for some patients, the majority of the cases will require some augmentation for the surface alignment plate. In some cases, the necessary augmentation is simply to close the space between the alignment plate 52 and the posterior surface of the femur when the knee is flexed, as shown in FIG. 2. In other cases, the surface of either the femur or the tibia has surface defects that compromise the stable support of the femoral positioner 50.

Figure 6:
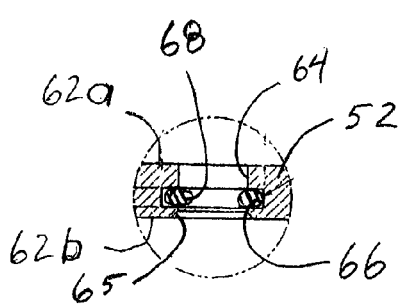
FIG. 6 is an enlarged cross-sectional view of a portion A in FIG. 5.
Figure 7:
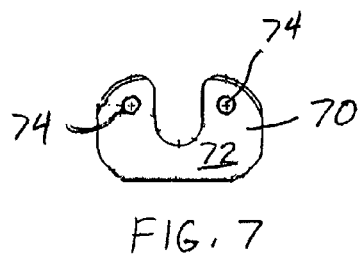
FIG. 7 is a top elevational view of an augment in accordance with one embodiment of the invention.
Figure 8:
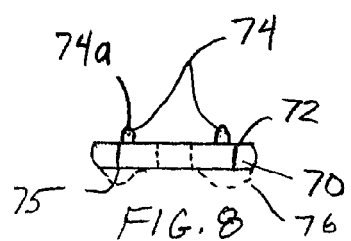
FIG. 8 is a side elevational view of the augment shown in FIG. 7.
Figure 9:
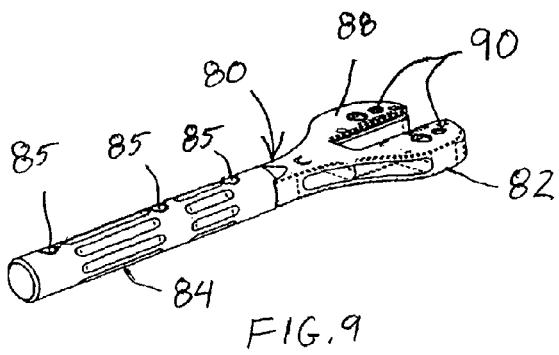
FIG. 9 is a perspective view of a spacer block in accordance with a further embodiment of the invention.
Figure 12:
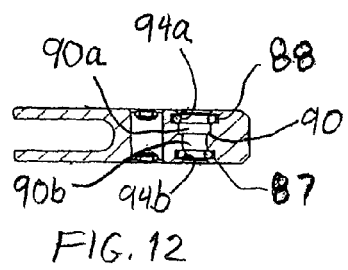
FIG. 12 is a cross-sectional view of the spacer block depicted in FIG. 9 taken along line B-B.
Figure 10:
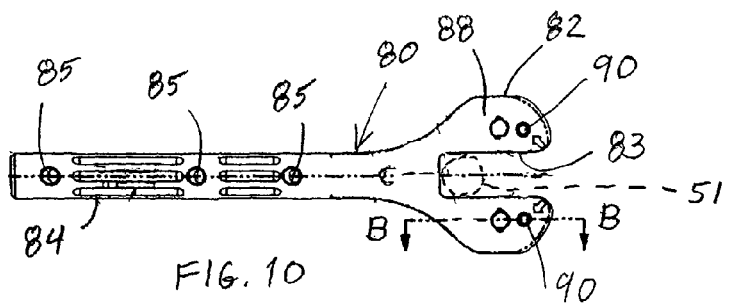
FIG. 10 is a top elevational view of the spacer block shown in FIG. 9.
Figure 11:
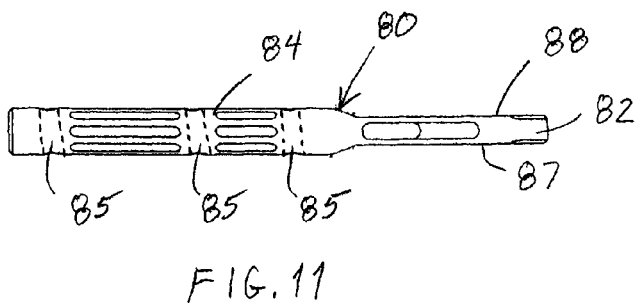
FIG. 11 is a side elevational view of the spacer block illustrated in FIG. 9

In either case, an augment, such as the augment 70 shown in FIGS. 7-8 may be necessary. The augment 70 includes a mating surface 72 and an opposite surface 75. The mating surface 72 contacts the surface alignment plate 52 of the positioner 50, while the opposite surface 75 contacts the bone. In the most basic case, the opposite surface 75 is flat and parallel to the mating surface 72. The thickness between these two surfaces can vary as necessary to fill the expected flexion/extension gap. Nominally, several augments 70 can be provided, each having different thicknesses. Where the augment 70 serves as a shim or spacer, the augment will normally be supported on the femoral-facing surface 62*a* of the positioner 50 (FIG. 6).

In other cases, the surface 75 of the augment 70 can include contours, such as the contours 76 shown in dashed lines. These contours are configured to match defects in the bone against which the augment bears. Where the defects are in the tibia, the augment will be mounted to the underside or the tibia-facing surface 62*b* of the positioner 50 (FIG. 6). The contours 76 fill the bone defects and ensure that the mating surface 72 will be supported in a proper parallel orientation.

In order to facilitate mounting and removal of the augment 70 from the positioner 50, means for removably coupling the components together are provided that incorporate a resilient member. In the preferred embodiment, the surface alignment plate 52 is provided with a pair of bores 64 on opposite sides of the notch 54. The augment 70 includes a mating pair of pins 74 that are sized to be received within a corresponding one of the bores. As shown in the detail of FIG. 6, each of the bores defines an internal groove 66 configured to receive an elastomeric O-ring 68. Each pin 74 is sized to pass through the bore 64 into frictional contact with the O-ring 68. The O-ring provides a tight elastomeric fit so that the pins are not easily dislodged from the bores during normal manipulation of the femoral positioner 50. Each pin can be provided with a groove (not shown) to receive the O-ring when the pin is properly positioned within the bore.

In the preferred embodiment, the O-ring groove 66 is offset toward the tibial surface 62*b*. The bore 64 has a diameter on either side of the groove 66 that provides a close running fit for the pin 74. The O-ring defines an inner diameter that is less than the diameter of the bore. Thus, the tip 74*a* of the pin can be tapered to facilitate being pushed through the O-ring 66. The base of the bore 64 at the tibial side can be provided with a chamfer 65 to further facilitate placement of the pin into the bore from the underside of the femoral positioner 50.

The augment 70 can also be used with a spacer block, such as the spacer block 80 shown in FIGS. 9-12. The spacer block 80 includes a spacer body 82 connected to a handle 84. The block defines a notch 83 therein that serves the same function as the notch 54 in the femoral positioner 50 discussed above. The handle 84 defines a number of angled bores 85 configured for receiving an alignment rod (not shown). The spacer block 80 can be used in a conventional manner to verify the flexion and extension gaps when the resection guide is mounted to the femur, or after the femoral implant has been mounted on the finished distal end of the femur.

In order to accommodate a variety of joint anatomies, the body 82 of the spacer block defines a pair of bores 90 passing from the tibial surface 87 to the femoral surface 88. The bores are sized to receive the pins 74 of an appropriate augment 70.

In accordance with the invention, the bores are provided with O-ring grooves and O-rings to firmly hold the pins within the bores.

In one feature of the embodiment, the bores 90 are provided with two grooves 92*a*, 92*b* and two O-rings 94*a*, 94*b*. One O-ring 94*a* is positioned near the femoral surface 88 and the other O-ring 94*b* is positioned near the tibial surface 87. It is contemplated that the pins 74 of the augment 70 have a predetermined height from the mating surface 72 that is calibrated to fit the bores 64 in the femoral positioner 50. Since the surface alignment plate 52 of the positioner is thinner than the body 82 of the spacer block 80, the height of the pins 74 is less than the thickness of the spacer block. Consequently, in order to orient an O-ring in a location where they can fully engage the pins, two O-rings 94*a*, 94*b* are provided, with a corresponding one offset to each surface of the spacer block.

In an alternative feature, the bore 90 can define a larger bore portion 90*a* and a smaller bore portion 90*b*. The larger portion 90*a* is adjacent the femoral surface 88, while the smaller portion 90*b* opens at the tibial surface 87.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, while the preferred embodiment calls for O-rings to provide the temporary fixation of the augment, the O-rings can be replaced with other resiliently gripping components. For instance, a slitted membrane can span the bores 64 or 90, wherein the pin penetrates the membrane, which then resiliently grasps the surface of the pin. Similarly, the O-rings can be replaced with a canted coil spring, similar to the canted spring coupling ring marketed by Bal-Seal Engineering. In this case, the engagement pins can define a groove to engage the canted coil spring.

What is claimed is:

1. A system for establishing a gap between a femur and a tibia at a knee joint, comprising:
    an instrument having (i) a positioning member that defines a femur facing side and a tibia facing side, said positioning member including a first coupler, and (ii) a connector member having a first mating feature;
    an augment having a second coupler that cooperates with said first coupler to fix said augment to said positioning member abutting either said femur facing side or said tibia facing side; and
    a femoral resection guide having a second mating feature that mates with said first mating feature of said instrument, the instrument, augment, and femoral resection guide configured such that when the system is assembled and the femoral resection guide is positioned on a femur, the instrument and the augment span a gap between a posterior surface of the femur and a proximal surface of a tibia.

2. The system of claim 1, wherein:
    said first coupler of said positioning member includes a bore having a resilient O-ring positioned therein, and
    said second coupler of said augment includes a pin that is in frictional contact with said O-ring.

3. The system of claim 2, wherein:
    said bore defines an internal groove, and
    said O-ring is positioned within said internal groove.

4. The system of claim 1, wherein:
    said first coupler of said positioning member includes a bore, and said second coupler of said augment includes a pin that is received within said bore.

5. The system of claim 1, wherein:
the tibia facing side is generally planar;
the augment includes an upper surface and a lower surface; and
the upper surface of the augment abuts the tibia facing side when the augment is fixed to the positioning member.

6. The system of claim 5, wherein the lower surface is contoured.

7. A system for establishing a gap between a femur and a tibia at a knee joint, comprising:
an instrument having a positioning member that includes a first coupler, said positioning member defining (i) a femur facing side, (ii) a tibia facing side, and (iii), a guide slot configured to receive an intramedullary pin;
an augment having a second coupler that cooperates with said first coupler to fix said augment to said positioning member abutting either said femur facing side or said tibia facing side; and
an intramedullary pin received within said guide slot of said positioning member of said instrument by movement of the guide slot relative to the intramedullary pin along an axis substantially parallel to at least one of the femur facing side and tibia facing side.

8. The system of claim 7, wherein:
said first coupler of said positioning member includes a bore having a resilient O-ring positioned therein, and
said second coupler of said augment includes a pin that is in frictional contact with said O-ring.

9. The system of claim 8, wherein:
said bore defines an internal groove, and
said O-ring is positioned within said internal groove.

10. The system of claim 7, wherein:
said first coupler of said positioning member includes a bore, and
said second coupler of said augment includes a pin that is received within said bore.

11. The system of claim 7, wherein said instrument further has a handle extending from said positioning member.

12. The system of claim 7, wherein:
the guide slot extends from the femur facing side to the tibia facing side and opens to a front portion of the positioning member;
the augment includes an upper surface and a lower surface; and
an augment slot extends from the upper surface to the lower surface and opens to a front portion of the augment, the augment slot positioned such that when the augment is fixed to the positioning member (i) the upper surface of the augment abuts the tibia facing side and (ii) the augment slot is aligned with the guide slot.

13. The system of claim 7, wherein:
the tibia facing side is generally planar;
the augment includes an upper surface and a lower surface; and
the upper surface of the augment abuts the tibia facing side when the augment is fixed to the positioning member.

14. A system for establishing a gap between a femur and a tibia at a knee joint, comprising:
an instrument having (i) a positioning member that defines a femur facing side and a tibia facing side, said positioning member including a first coupler, and (ii) a connector member having a first mating feature;
an augment having a second coupler that cooperates with said first coupler to fix said augment to said positioning member; and
a femoral resection guide having a second mating feature that mates with said first mating feature of said instrument,
wherein said first coupler of said positioning member includes a bore having a resilient O-ring positioned therein,
said second coupler of said augment includes a pin that is in frictional contact with said O-ring, and
the instrument, augment, and femoral resection guide are configured such that when the system is assembled and the femoral resection guide is positioned on a femur, the instrument and the augment span a gap between the femur and a tibia.

15. The system of claim 14, wherein:
said bore defines an internal groove, and
said O-ring is positioned within said internal groove.

16. The system of claim 14, wherein:
the tibia facing side is generally planar;
the augment includes an upper surface and a lower surface; and
the upper surface of the augment abuts the tibia facing side when the augment is fixed to the positioning member.

17. The system of claim 16, wherein the lower surface is contoured.

18. A system for establishing a gap between a femur and a tibia at a knee joint, comprising:
an instrument having a positioning member that includes a first coupler, said positioning member defining (i) a femur facing side, (ii) a tibia facing side, and (iii), a guide slot configured to receive an intramedullary pin;
an augment having a second coupler that cooperates with said first coupler to fix said augment to said positioning member; and
an intramedullary pin received within said guide slot of said positioning member of said instrument by movement of the guide slot relative to the intramedullary pin along an axis substantially parallel to at least one of the femur facing side and tibia facing side,
wherein said first coupler of said positioning member includes a bore having a resilient O-ring positioned therein, and
said second coupler of said augment includes a pin that is in frictional contact with said O-ring.

19. The system of claim 18, wherein:
said bore defines an internal groove, and
said O-ring is positioned within said internal groove.

20. The system of claim 18, wherein said instrument further has a handle extending from said positioning member.

* * * * *